(12) United States Patent
Yoshizawa et al.

(10) Patent No.: US 9,588,125 B2
(45) Date of Patent: Mar. 7, 2017

(54) METHOD AND SYSTEM FOR ANALYZING PROTEIN OR PEPTIDE

(71) Applicant: SHIMADZU CORPORATION, Kyoto-shi, Kyoto (JP)

(72) Inventors: Akiyasu Yoshizawa, Kyoto (JP); Takayuki Yoshimori, Nerima-ku (JP); Yuki Ohta, Kawasaki (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/212,833

(22) Filed: Mar. 14, 2014

(65) Prior Publication Data
US 2014/0357501 A1    Dec. 4, 2014

(30) Foreign Application Priority Data
May 29, 2013    (JP) ................................. 2013-113070

(51) Int. Cl.
*C12Q 1/37*        (2006.01)
*G01N 33/68*       (2006.01)

(52) U.S. Cl.
CPC .......... *G01N 33/6848* (2013.01); *C12Q 1/37* (2013.01)

(58) Field of Classification Search
CPC .............................. C12Q 1/37; G01N 33/6848
See application file for complete search history.

(56) References Cited

U.S. PATENT DOCUMENTS

| | | | | |
|---|---|---|---|---|
| 7,960,339 B2 * | 6/2011 | Blondelle | ........... | C07K 14/4723 514/2.3 |
| 2005/0084901 A1 * | 4/2005 | Everett | ............... | G01N 33/6848 435/7.1 |
| 2006/0029977 A1 * | 2/2006 | Everett | ............... | G01N 33/6848 435/7.1 |

FOREIGN PATENT DOCUMENTS

| | | |
|---|---|---|
| JP | 9510780 A | 10/1997 |
| WO | 9525281 A1 | 9/1995 |

OTHER PUBLICATIONS

Bennett et al. Complete Amino Acid Analysis of Peptides and Proteins after Hydrolysis by a Mixture of Sepharose-Bound Peptides. Biochem J. 1972, vol. 129, pp. 695-701.*
Gundry et al. Preparation of Proteins and Peptides for Mass Spectrometry Analysis in a Bottom-Up Proteomics Workflow. Curr Protoc Mol Biol. Oct. 2009. Chapter Unit 10.25, pp. 1-29.*
Kato, "Amino-san Bunseki wo Mochiita Seikaku na Tanpakushitsu Teiryou-hou—Shinraisei no Takai Teiryou-hou no Kaihatsu to 'C Hannousei Tanpaku Hyoujun-eki' Kaihatsu he no Ouyou (An Accurate Protein Quantification Based on Amino Acid Analysis—Development of Protein Quantification Method Applied to the Certification of C-Reactive Protein Standard Solution)", The National Institute of Advanced Industrial Science and Technology, [Searched on Mar. 1, 2013], Internet <URL: http://www.aist.go.jp/aist_j/aistinfo/aist_today/vol0 8_09/vol08_09_p18.pdf>.
Watanabe et al., "UF-Amino Station ni yoru Amino-san no Taseibun Issei Kousoku Bunseki—Shokuhin Bunseki e no Ouyou (High-Speed Simultaneous Analysis of Multiple Amino-Acid Components by UF-Amino Station—Application to Food Analysis)", Shimadzu Hyouron Henshuu-bu, Shimadzu Hyouron (*Shimadzu Review*), Sep. 30, 2012, pp. 47-54, vol. 69, Nos. 1/2.
John Hwa et al., "Structure and function in rhodopsin: Mass spectrometric identification of the abnormal intradiscal disulfide bond in misfolded retinitis pigmentosa mutants", *Proceedings of the National Academy of Sciences*, Apr. 24, 2001, pp. 4872-4876 vol. 98, No. 9.
Christine C. Wu et al., "A method for the comprehensive proteomic analysis of membrane proteins", *nature biotechnology*, May 2003, pp. 532-538, vol. 21.
Dimitrios G. Papasotiriou et al., "Peptide Mass Fingerprinting after Less Specific In-Gel Proteolysis Using MALDI-LTQ-Orbitrap and 4-Chloro-α-cyanocinnamic Acid", *Journal of proteome research*, 2010, pp. 2619-2629 vol. 9.
Evgeniy V. Petrotchenko et al., "Use of Proteinase K Nonspecific Digestion for Selective and Comprehensive Identification of Interpeptide Cross-links: Application to Prion Proteins", *Molecular & Cellular Proteomics*, 11 (7), 2012, 10.1074/mcp.M111.013524.
Hirayama, "Structural Studies of Proteins by Mass Spectrometry", The Mass Spectrometry Society of Japan, 2012, vol. 60, No. 5, pp. 51-64, 14 pages in total.
Li et al, "Sequence-ion Enhancement of Peptides Digested with Proteinase K", Rapid Communications in Mass Spectrometry, 1994, vol. 8, No. 10, pp. 833-836, 4 pages in total.

(Continued)

*Primary Examiner* — Marcela M Cordero Garcia
(74) *Attorney, Agent, or Firm* — Sughrue Mion, PLLC

(57) ABSTRACT

A peptide is cleaved at various bonding sites into oligopeptides or similar fragments by digestion using proteinase K (S3). The obtained fragments are separated according to their kinds by reversed-phase chromatography and fractionated (S4), and each fragment is subjected to mass spectrometry to determine its mass (S6). For each peptide fragment, an amino-acid composition is calculated from the measured mass, and amino-acid sequence candidates are deduced from that composition. The amino-acid sequence candidates of the other peptide fragments are searched for a fragment having an overlapping portion available for combining two peptide fragments to obtain amino-acid sequence candidates of the original peptide (S7). The masses of the amino-acid sequence candidates are compared with a measured mass derived from a result of mass spectrometry of the original peptide to select a correct sequence (S6 and S8).

7 Claims, 6 Drawing Sheets

(56) References Cited

OTHER PUBLICATIONS

"Proteinase K, recombinant, PCR Grade", Roche Diagnostics, Nov. 2005, URL, https://pim-eservices.roche.com/LifeScience/Document/af651c3c-95ed-e311-98a1-00215a9b0ba8 (document showing well-known technology), 2 pages in total.
Communication dated Apr. 5, 2016, from the Japanese Patent Office issued in counterpart application No. 2013-113070.

* cited by examiner

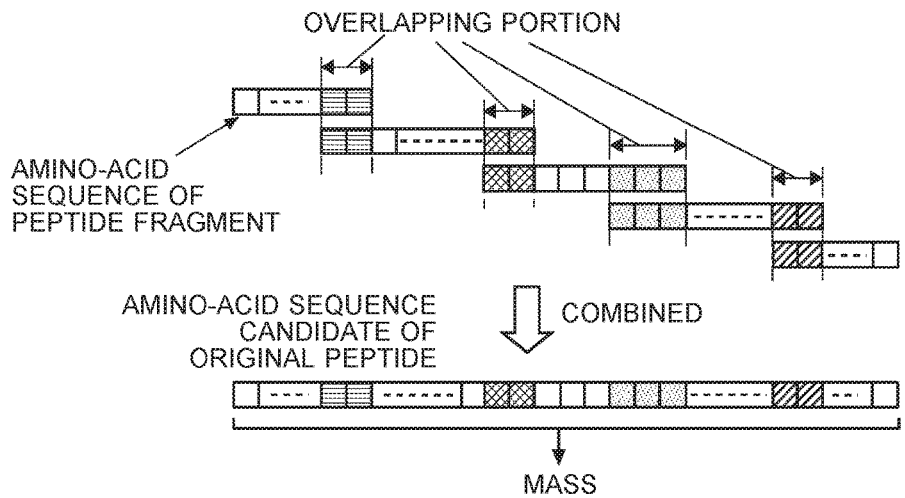

(a) INSULIN

[MALWMRLLPLLALLALWGPDPAAAFVNQHLCGSHLVEALYLVCGERGFFYTPKTRREAED
LQVGQVELGGGPGAGSLQPLALEGSLQKRGIVEQCCTSICSLYQLENYCN] SEQ ID NO: 1

⇩ CLEAVED

[MALWMR] SEQ ID NO: 2
[LLPLLALLALWGPDPAAAFVNQHLCGSHLVEALYLVCGER] SEQ ID NO: 3
[GFFYTPK] SEQ ID NO: 4
[TR]
[R]
[EAEDLQVGQVELGGGPGAGSLQPLALEGSLQK] SEQ ID NO: 5
[GIVEQCCTSICSLYQLENYCN] SEQ ID NO: 6

(b) [GFFYTPK] SEQ ID NO: 4

⇩ FRAGMENTED

COMPOSITION

SEQ ID NO: 7 [GFFY] ----- F2G1Y1
SEQ ID NO: 8 [FFYTP] ----- F2P1T1Y1
SEQ ID NO: 9 [FYTP] ----- F1P1T1Y1
              [TPK] ----- K1P1T1

(a) COMPOSITION: F2G1Y1 → POSSIBLE SEQUENCES:
[GFFY] SEQ ID NO: 7
[GFYF] SEQ ID NO: 10
[GYFF] SEQ ID NO: 11
[FGFY] SEQ ID NO: 12
[FGYF] SEQ ID NO: 13
[YGFF] SEQ ID NO: 14
[FFGY] SEQ ID NO: 15
[FYGF] SEQ ID NO: 16
[YFGF] SEQ ID NO: 17
[FFYG] SEQ ID NO: 18
[FYFG] SEQ ID NO: 19
[YFFG] SEQ ID NO: 20

(b) COMPOSITION: F1P1T1Y1 → POSSIBLE SEQUENCES:
[FYTP] SEQ ID NO: 21
[FYPT] SEQ ID NO: 22
[FTYP] SEQ ID NO: 23
[FPYT] SEQ ID NO: 24
⋮

Fig. 7

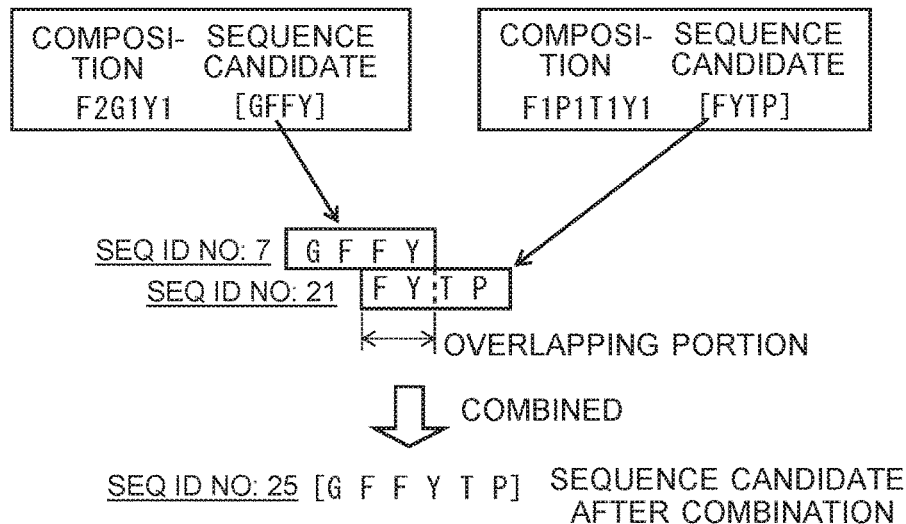

Fig. 8

```
                                COMPOSITION
SEQ ID NO: 25 [GFFYTP]  ---- F2G1P1T1Y1
SEQ ID NO: 26 [GFFYPT]  ---- F2G1P1T1Y1
SEQ ID NO: 27 [GFFYFTP] ---- F3G1P1T1Y1
SEQ ID NO: 28 [GFFYFPT] ---- F3G1P1T1Y1
SEQ ID NO: 29 [GFFYPFT] ---- F3G1P1T1Y1
SEQ ID NO: 30 [GFFYTFP] ---- F3G1P1T1Y1
SEQ ID NO: 31 [GFFYPTF] ---- F3G1P1T1Y1
SEQ ID NO: 32 [GFFYTPF] ---- F3G1P1T1Y1

SEQ ID NO: 33 [GFYFTP]  ---- F2G1P1T1Y1
SEQ ID NO: 34 [GFYFPT]  ---- F2G1P1T1Y1
SEQ ID NO: 35 [GFYFYTP] ---- F2G1P1T1Y2
SEQ ID NO: 36 [GFYFYPT] ---- F2G1P1T1Y2
SEQ ID NO: 37 [GFYFTYP] ---- F2G1P1T1Y2
SEQ ID NO: 38 [GFYFPYT] ---- F2G1P1T1Y2
SEQ ID NO: 39 [GFYFTPY] ---- F2G1P1T1Y2
SEQ ID NO: 40 [GFYFPTY] ---- F2G1P1T1Y2

SEQ ID NO: 41 [GYFFYTP] ---- F2G1P1T1Y2
SEQ ID NO: 42 [GYFFYPT] ---- F2G1P1T1Y2
SEQ ID NO: 43 [GYFFTYP] ---- F2G1P1T1Y2
SEQ ID NO: 44 [GYFFPYT] ---- F2G1P1T1Y2
SEQ ID NO: 45 [GYFFTPY] ---- F2G1P1T1Y2
SEQ ID NO: 46 [GYFFPTY] ---- F2G1P1T1Y2
```

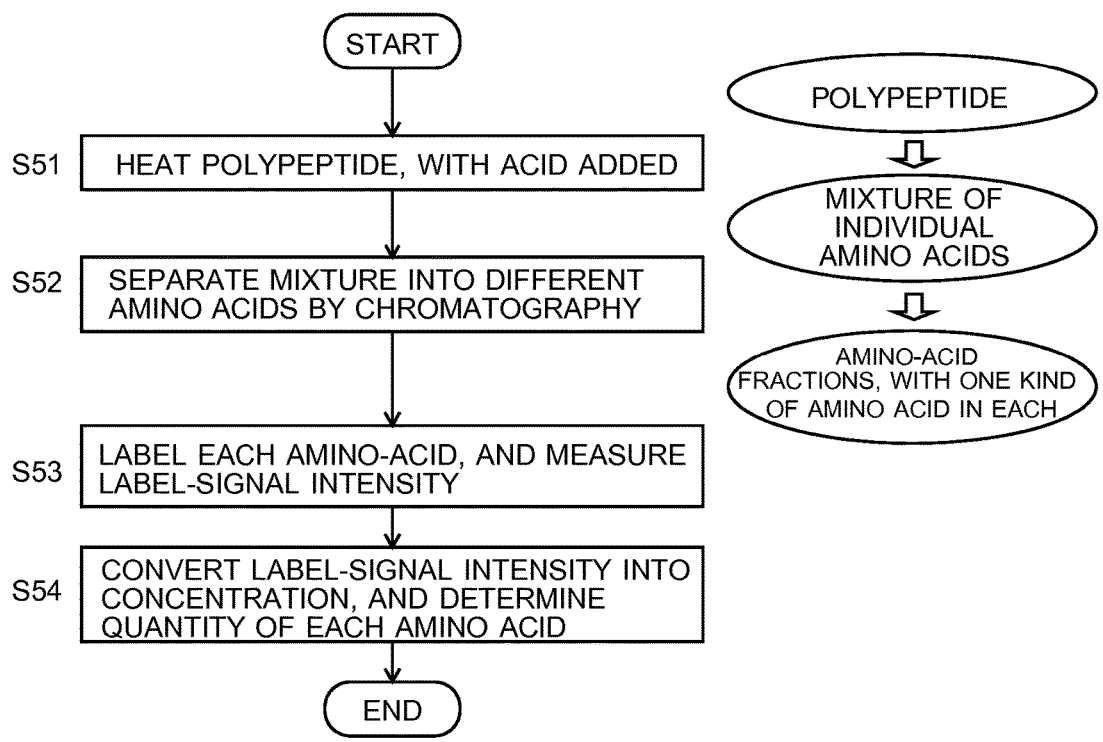

SEQUENCE LISTING

```
<160> NUMBER OF SEQ ID NOS: 46

<210> SEQ ID NO 1
<211> LENGTH: 110
<212> TYPE: PRT
<213> ORGANISM: Artificial Sequence
<220> FEATURE:
<223> OTHER INFORMATION: insulin peptide

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
                100                 105                 110

<210> SEQ ID NO 2
<211> LENGTH: 6
<212> TYPE: PRT
<213> ORGANISM: Artificial Sequence
<220> FEATURE:
<223> OTHER INFORMATION: peptide

<400> SEQUENCE: 2

Met Ala Leu Trp Met Arg
1               5

<210> SEQ ID NO 3
<211> LENGTH: 40
<212> TYPE: PRT
<213> ORGANISM: Artificial Sequence
<220> FEATURE:
<223> OTHER INFORMATION: peptide

<400> SEQUENCE: 3

Leu Leu Pro Leu Leu Ala Leu Leu Ala Leu Trp Gly Pro Asp Pro Ala
1               5                   10                  15

Ala Ala Phe Val Asn Gln His Leu Cys Gly Ser His Leu Val Glu Ala
            20                  25                  30

Leu Tyr Leu Val Cys Gly Glu Arg
        35                  40
```

```
<210> SEQ ID NO 4
<211> LENGTH: 7
<212> TYPE: PRT
<213> ORGANISM: Artificial Sequence
<220> FEATURE:
<223> OTHER INFORMATION: peptide

<400> SEQUENCE: 4

Gly Phe Phe Tyr Thr Pro Lys
1               5

<210> SEQ ID NO 5
<211> LENGTH: 32
<212> TYPE: PRT
<213> ORGANISM: Artificial Sequence
<220> FEATURE:
<223> OTHER INFORMATION: peptide

<400> SEQUENCE: 5

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln Lys
            20                  25                  30

<210> SEQ ID NO 6
<211> LENGTH: 21
<212> TYPE: PRT
<213> ORGANISM: Artificial Sequence
<220> FEATURE:
<223> OTHER INFORMATION: peptide

<400> SEQUENCE: 6

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 7
<211> LENGTH: 4
<212> TYPE: PRT
<213> ORGANISM: Artificial Sequence
<220> FEATURE:
<223> OTHER INFORMATION: peptide

<400> SEQUENCE: 7

Gly Phe Phe Tyr
1

<210> SEQ ID NO 8
<211> LENGTH: 5
<212> TYPE: PRT
<213> ORGANISM: Artificial Sequence
<220> FEATURE:
<223> OTHER INFORMATION: peptide

<400> SEQUENCE: 8

Phe Phe Tyr Thr Pro
1               5

<210> SEQ ID NO 9
<211> LENGTH: 4
<212> TYPE: PRT
<213> ORGANISM: Artificial Sequence
<220> FEATURE:
<223> OTHER INFORMATION: peptide
```

```
<400> SEQUENCE: 9

Phe Tyr Thr Pro
1

<210> SEQ ID NO 10
<211> LENGTH: 4
<212> TYPE: PRT
<213> ORGANISM: Artificial Sequence
<220> FEATURE:
<223> OTHER INFORMATION: peptide

<400> SEQUENCE: 10

Gly Phe Tyr Phe
1

<210> SEQ ID NO 11
<211> LENGTH: 4
<212> TYPE: PRT
<213> ORGANISM: Artificial Sequence
<220> FEATURE:
<223> OTHER INFORMATION: peptide

<400> SEQUENCE: 11

Gly Tyr Phe Phe
1

<210> SEQ ID NO 12
<211> LENGTH: 4
<212> TYPE: PRT
<213> ORGANISM: Artificial Sequence
<220> FEATURE:
<223> OTHER INFORMATION: peptide

<400> SEQUENCE: 12

Phe Gly Phe Tyr
1

<210> SEQ ID NO 13
<211> LENGTH: 4
<212> TYPE: PRT
<213> ORGANISM: Artificial Sequence
<220> FEATURE:
<223> OTHER INFORMATION: peptide

<400> SEQUENCE: 13

Phe Gly Tyr Phe
1

<210> SEQ ID NO 14
<211> LENGTH: 4
<212> TYPE: PRT
<213> ORGANISM: Artificial Sequence
<220> FEATURE:
<223> OTHER INFORMATION: peptide

<400> SEQUENCE: 14

Tyr Gly Phe Phe
1

<210> SEQ ID NO 15
<211> LENGTH: 4
<212> TYPE: PRT
<213> ORGANISM: Artificial Sequence
<220> FEATURE:
<223> OTHER INFORMATION: peptide

<400> SEQUENCE: 15
```

Phe Phe Gly Tyr
1

<210> SEQ ID NO 16
<211> LENGTH: 4
<212> TYPE: PRT
<213> ORGANISM: Artificial Sequence
<220> FEATURE:
<223> OTHER INFORMATION: peptide

<400> SEQUENCE: 16

Phe Tyr Gly Phe
1

<210> SEQ ID NO 17
<211> LENGTH: 4
<212> TYPE: PRT
<213> ORGANISM: Artificial Sequence
<220> FEATURE:
<223> OTHER INFORMATION: peptide

<400> SEQUENCE: 17

Tyr Phe Gly Phe
1

<210> SEQ ID NO 18
<211> LENGTH: 4
<212> TYPE: PRT
<213> ORGANISM: Artificial Sequence
<220> FEATURE:
<223> OTHER INFORMATION: peptide

<400> SEQUENCE: 18

Phe Phe Tyr Gly
1

<210> SEQ ID NO 19
<211> LENGTH: 4
<212> TYPE: PRT
<213> ORGANISM: Artificial Sequence
<220> FEATURE:
<223> OTHER INFORMATION: peptide

<400> SEQUENCE: 19

Phe Tyr Phe Gly
1

<210> SEQ ID NO 20
<211> LENGTH: 4
<212> TYPE: PRT
<213> ORGANISM: Artificial Sequence
<220> FEATURE:
<223> OTHER INFORMATION: peptide

<400> SEQUENCE: 20

Tyr Phe Phe Gly
1

<210> SEQ ID NO 21
<211> LENGTH: 4
<212> TYPE: PRT
<213> ORGANISM: Artificial Sequence
<220> FEATURE:
<223> OTHER INFORMATION: peptide

<400> SEQUENCE: 21

Phe Tyr Thr Pro
1

<210> SEQ ID NO 22
<211> LENGTH: 4
<212> TYPE: PRT
<213> ORGANISM: Artificial Sequence
<220> FEATURE:
<223> OTHER INFORMATION: peptide

<400> SEQUENCE: 22

Phe Tyr Pro Thr
1

<210> SEQ ID NO 23
<211> LENGTH: 4
<212> TYPE: PRT
<213> ORGANISM: Artificial Sequence
<220> FEATURE:
<223> OTHER INFORMATION: peptide

<400> SEQUENCE: 23

Phe Thr Tyr Pro
1

<210> SEQ ID NO 24
<211> LENGTH: 4
<212> TYPE: PRT
<213> ORGANISM: Artificial Sequence
<220> FEATURE:
<223> OTHER INFORMATION: peptide

<400> SEQUENCE: 24

Phe Pro Tyr Thr
1

<210> SEQ ID NO 25
<211> LENGTH: 6
<212> TYPE: PRT
<213> ORGANISM: Artificial Sequence
<220> FEATURE:
<223> OTHER INFORMATION: peptide

<400> SEQUENCE: 25

Gly Phe Phe Tyr Thr Pro
1               5

<210> SEQ ID NO 26
<211> LENGTH: 6
<212> TYPE: PRT
<213> ORGANISM: Artificial Sequence
<220> FEATURE:
<223> OTHER INFORMATION: peptide

<400> SEQUENCE: 26

Gly Phe Phe Tyr Pro Thr
1               5

<210> SEQ ID NO 27
<211> LENGTH: 7
<212> TYPE: PRT
<213> ORGANISM: Artificial Sequence
<220> FEATURE:
<223> OTHER INFORMATION: peptide

<400> SEQUENCE: 27

Gly Phe Phe Tyr Phe Thr Pro

```
1               5

<210> SEQ ID NO 28
<211> LENGTH: 7
<212> TYPE: PRT
<213> ORGANISM: Artificial Sequence
<220> FEATURE:
<223> OTHER INFORMATION: peptide

<400> SEQUENCE: 28

Gly Phe Phe Tyr Phe Pro Thr
1               5

<210> SEQ ID NO 29
<211> LENGTH: 7
<212> TYPE: PRT
<213> ORGANISM: Artificial Sequence
<220> FEATURE:
<223> OTHER INFORMATION: peptide

<400> SEQUENCE: 29

Gly Phe Phe Tyr Pro Phe Thr
1               5

<210> SEQ ID NO 30
<211> LENGTH: 7
<212> TYPE: PRT
<213> ORGANISM: Artificial Sequence
<220> FEATURE:
<223> OTHER INFORMATION: peptide

<400> SEQUENCE: 30

Gly Phe Phe Tyr Thr Phe Pro
1               5

<210> SEQ ID NO 31
<211> LENGTH: 7
<212> TYPE: PRT
<213> ORGANISM: Artificial Sequence
<220> FEATURE:
<223> OTHER INFORMATION: peptide

<400> SEQUENCE: 31

Gly Phe Phe Tyr Pro Thr Phe
1               5

<210> SEQ ID NO 32
<211> LENGTH: 7
<212> TYPE: PRT
<213> ORGANISM: Artificial Sequence
<220> FEATURE:
<223> OTHER INFORMATION: peptide

<400> SEQUENCE: 32

Gly Phe Phe Tyr Thr Pro Phe
1               5

<210> SEQ ID NO 33
<211> LENGTH: 6
<212> TYPE: PRT
<213> ORGANISM: Artificial Sequence
<220> FEATURE:
<223> OTHER INFORMATION: peptide

<400> SEQUENCE: 33

Gly Phe Tyr Phe Thr Pro
1               5
```

<210> SEQ ID NO 34
<211> LENGTH: 6
<212> TYPE: PRT
<213> ORGANISM: Artificial Sequence
<220> FEATURE:
<223> OTHER INFORMATION: peptide

<400> SEQUENCE: 34

Gly Phe Tyr Phe Pro Thr
1               5

<210> SEQ ID NO 35
<211> LENGTH: 7
<212> TYPE: PRT
<213> ORGANISM: Artificial Sequence
<220> FEATURE:
<223> OTHER INFORMATION: peptide

<400> SEQUENCE: 35

Gly Phe Tyr Phe Tyr Thr Pro
1               5

<210> SEQ ID NO 36
<211> LENGTH: 7
<212> TYPE: PRT
<213> ORGANISM: Artificial Sequence
<220> FEATURE:
<223> OTHER INFORMATION: peptide

<400> SEQUENCE: 36

Gly Phe Tyr Phe Tyr Pro Thr
1               5

<210> SEQ ID NO 37
<211> LENGTH: 7
<212> TYPE: PRT
<213> ORGANISM: Artificial Sequence
<220> FEATURE:
<223> OTHER INFORMATION: peptide

<400> SEQUENCE: 37

Gly Phe Tyr Phe Thr Tyr Pro
1               5

<210> SEQ ID NO 38
<211> LENGTH: 7
<212> TYPE: PRT
<213> ORGANISM: Artificial Sequence
<220> FEATURE:
<223> OTHER INFORMATION: peptide

<400> SEQUENCE: 38

Gly Phe Tyr Phe Pro Tyr Thr
1               5

<210> SEQ ID NO 39
<211> LENGTH: 7
<212> TYPE: PRT
<213> ORGANISM: Artificial Sequence
<220> FEATURE:
<223> OTHER INFORMATION: peptide

<400> SEQUENCE: 39

Gly Phe Tyr Phe Thr Pro Tyr
1               5

<210> SEQ ID NO 40
<211> LENGTH: 7
<212> TYPE: PRT
<213> ORGANISM: Artificial Sequence
<220> FEATURE:
<223> OTHER INFORMATION: peptide

<400> SEQUENCE: 40

Gly Phe Tyr Phe Pro Thr Tyr
1               5

<210> SEQ ID NO 41
<211> LENGTH: 7
<212> TYPE: PRT
<213> ORGANISM: Artificial Sequence
<220> FEATURE:
<223> OTHER INFORMATION: peptide

<400> SEQUENCE: 41

Gly Tyr Phe Phe Tyr Thr Pro
1               5

<210> SEQ ID NO 42
<211> LENGTH: 7
<212> TYPE: PRT
<213> ORGANISM: Artificial Sequence
<220> FEATURE:
<223> OTHER INFORMATION: peptide

<400> SEQUENCE: 42

Gly Tyr Phe Phe Tyr Pro Thr
1               5

<210> SEQ ID NO 43
<211> LENGTH: 7
<212> TYPE: PRT
<213> ORGANISM: Artificial Sequence
<220> FEATURE:
<223> OTHER INFORMATION: peptide

<400> SEQUENCE: 43

Gly Tyr Phe Phe Thr Tyr Pro
1               5

<210> SEQ ID NO 44
<211> LENGTH: 7
<212> TYPE: PRT
<213> ORGANISM: Artificial Sequence
<220> FEATURE:
<223> OTHER INFORMATION: peptide

<400> SEQUENCE: 44

Gly Tyr Phe Phe Pro Tyr Thr
1               5

<210> SEQ ID NO 45
<211> LENGTH: 7
<212> TYPE: PRT
<213> ORGANISM: Artificial Sequence
<220> FEATURE:
<223> OTHER INFORMATION: peptide

<400> SEQUENCE: 45

Gly Tyr Phe Phe Thr Pro Tyr
1               5

```
<210> SEQ ID NO 46
<211> LENGTH: 7
<212> TYPE: PRT
<213> ORGANISM: Artificial Sequence
<220> FEATURE:
<223> OTHER INFORMATION: peptide

<400> SEQUENCE: 46

Gly Tyr Phe Phe Pro Thr Tyr
1               5
```

METHOD AND SYSTEM FOR ANALYZING PROTEIN OR PEPTIDE

TECHNICAL FIELD

The present invention relates to a method and a system for analyzing a protein or peptide in order to deduce the amino-acid composition of the protein or peptide and/or determine the quantities of amino acids constituting the protein or peptide.

BACKGROUND ART

Amino acids are basic structural units of proteins and peptides. They can also independently act as free amino acids which have various functions, such as controllers of bodily functions or taste components in foods. Therefore, compositional and quantitative analyses of amino acids in samples are extremely important in many technical areas, such as biochemistry, medical care, as well as research and developments of drugs, food and beverages.

FIG. 9 is a flowchart showing a conventional and common procedure of a quantitative analysis of amino acids in a protein.

In the first stage, an acid solution is added to polypeptides which have been produced by breaking down a protein using an appropriate enzyme or another means, after which the polypeptides are heated to break down them to amino acids (Step S51). The obtained mixture of various amino acids is separated according to the kinds of amino acids by an appropriate separation technique, such as liquid chromatography (Step S52). The separated amino acids are individually labelled, and the respective label signals are measured (Step S53). Ultimately, the intensities of the measured label signals are converted into concentrations, for example, by referring to calibration curves prepared beforehand to determine the quantity of each amino acid (Step S54).

Previously, a ninhydrin reaction was used for the labelling of amino acids in Step S53. Currently, a fluorescent dye label is used in many cases. The previously described method for the quantitative analysis of amino acids is an adequately established technique and can yield highly reliable results in quantitative determination. For example, Non-Patent Document 1 discloses a technique for determining the concentration of a protein by the previously described analyzing method. Another example is an amino acid analyzer disclosed in Non-Patent Document 2, in which a measurement corresponding to Step S53 is performed with a mass spectrometer to reduce the processing time as well as improve the measurement accuracy. A technique for breaking down proteins without using the acidic hydrolysis in Step S51 has also been proposed; specifically, the technique simultaneously uses several kinds of protein digestive enzymes (proteases) to completely digest a protein into isolated amino acids.

Thus, various improvements have been made to the amino acid analyzing method according to the procedure shown in FIG. 9, so as to reduce the processing time or improve the measurement accuracy. In any of those variations, the first step is a pretreatment for completely breaking down a sample (i.e. a protein or peptide) into isolated amino acids, and in most cases, acidic hydrolysis is used in this pretreatment.

In the acidic hydrolysis, the break down of polypeptide into amino acids is performed under extreme conditions; i.e. the sample is heated after a high-concentration acid solution is added (as a typical example, the treatment is performed at 110 degrees Celsius for 24 hours, using a 6 mol/L hydrochloric acid solution). Such a dangerous task requires a skilled worker with appropriate experience. Another problem results from the fact that amino acids vary in stability under high temperature; for some kinds of amino acids, the heat reaction time should be short to achieve high recovery efficiency while a long heat reaction time is desired for other kinds of amino acids to achieve high recovery efficiency. Therefore, to exhaustively recover as many kinds of amino acids as possible, it is necessary to perform additional cumbersome tasks, such as dividing the sample into a plurality of lots and changing the heat reaction time for each lot. In some cases, the required heat reaction time may be as long as 72 hours. Thus, the acidic hydrolysis of a protein requires an extremely cumbersome and time-consuming task which can be conducted only by a select group of workers.

The technique of using microwave heating for acidic hydrolysis of polypeptides has also been proposed, which can reduce the heat reaction time. However, such a technique requires a dedicated, non-versatile apparatus for the pretreatment. Furthermore, the handling and operation of such a special apparatus also requires a skilled worker with appropriate experience.

The amino acid analysis which uses acidic hydrolysis for the pretreatment has a more fundamental problem relating to the accuracy of the analysis: An acidic hydrolysis is such a strong chemical reaction that a considerable number of amino acids undergo influences during the reaction of acidic hydrolysis. For example, cysteine becomes structurally unstable due to the reaction of acidic hydrolysis and hence cannot be recovered in a stable quantity. Asparagine is broken down into asparagine acid by acidic hydrolysis, which means that, if asparagine acid has been found in the products of the acidic hydrolysis, it is impossible to determine whether the asparagine acid has originated directly from a peptide or indirectly via asparagine. The same problem also occurs in the case of glutamine, which is broken down into glutamine acid by acidic hydrolysis. Tryptophan is completely broken down by the acidic hydrolysis reaction, and therefore, its quantity cannot be determined. Thus, the quantitative determination is uncertain or virtually impossible for at least six amino acids (cysteine, asparagine, asparagine acid, glutamine, glutamine acid and tryptophan) out of the twenty amino acids which are known as the constituents of proteins. The previously described techniques can still be applied for a sample which contains none of the six amino acids. However, it is inappropriate to use those techniques for a sample which contains any one of the six amino acids or an unknown sample which contains unknown kinds of amino acids.

The method in which the break down of polypeptides is achieved by the use of several kinds of protein digestive enzymes at a time instead of the acidic hydrolysis is free from the aforementioned drawbacks specific to the acidic hydrolysis. However, the biochemical treatment used in the method is extremely complex, and a considerably strict adjustment of the measurement conditions is required to completely digest a polypeptide into isolated amino acids. The adjustment task is so complex and difficult that it needs a worker with select skills and experience.

BACKGROUND ART DOCUMENT

Non-Patent Document

Non-Patent Document 1: Kato, "Amino-san Bunseki wo Mochiita Seikaku na Tanpakushitsu Teiryou-hou—Shinraisei no Takai Teiryou-hou no Kaihatsu to 'C Hannousei Tanpaku Hyoujun-eki' Kaihatsu he no Ouyou (An Accurate Protein Quantification Based on Amino Acid Analysis—Development of Protein Quantification Method Applied to the Certification of C-Reactive Protein Standard Solution)", The National Institute of Advanced Industrial Science and Technology, [Searched on Mar. 1, 2013], Internet Non-Patent Document 2: Watanabe et al., "UF-Amino Station ni yoru Amino-san no Taseibun Issei Kousoku Bunseki—Shokuhin Bunseki e no Ouyou (High-Speed Simultaneous Analysis of Multiple Amino-Acid Components by UF-Amino Station—Application to Food Analysis)", Shimadzu Hyouron Henshuu-bu, Shimadzu Hyouron (*Shimadzu Review*), Vol. 69, Nos. 1/2, Sep. 30, 2012, pp. 47-54

SUMMARY OF THE INVENTION

Problem to be Solved by the Invention

The present invention has been developed to solve the previously described problems. Its first objective is to provide a method and a system for analyzing a protein or peptide which can collect amino-acid information that cannot be obtained by the conventional method using acidic hydrolysis, and which can determine the amino-acid composition of a protein or peptide and/or the quantities of amino acids in a protein or peptide with high accuracy or high reproducibility.

The second objective of the present invention is to provide a method and a system for analyzing a protein or peptide which only requires a simple task for the sample pretreatment and hence barely allows incorrect operations or difficulties even if the worker is poorly skilled or experienced, and which does not require any special apparatus or device.

Means for Solving the Problem

A large portion of the problems in the previously described analyzing techniques arise from the use of the acidic hydrolysis for the break down of peptides. Given this problem, the present inventors have paid attention to the broad-spectrum endopeptidase (the typical example is proteinase K) as a peptide break down technique that can replace acidic hydrolysis. Proteinase K, which is a serine peptidase derived from a fungus (*Engyodontium album*), has an extremely wide range of substrate specificity and can break all kinds of peptide bonds at considerably high reaction rates. Due to such characteristics, proteinase K has been mainly used for inactivating unwanted proteins mixed in a nucleic-acid preparation (e.g. for inactivating a nuclease, i.e. an enzyme that cleaves nucleic acids) or for similar purposes in the biochemical area. Paying attention to such characteristics, the present inventors have experimentally confirmed that a broad-spectrum endopeptidase can be used for breaking down a peptide to be analyzed into analyzable fragments. The present invention has thus been conceived.

The present invention aimed at solving the previously described problems provides a method for analyzing a protein or peptide for determining at least an amino-acid composition of a protein or peptide or quantities of amino acids in a protein or peptide, including:

a) a fragmentation step, in which a peptide originating from an analysis target which is either a peptide or a protein is broken down into peptide fragments by breaking peptide bonds using a broad-spectrum endopeptidase; and b) a separation step, in which a mixture of the peptide fragments obtained in the fragmentation step is separated according to the kinds of peptide fragments and collected in the form of fractions, each fraction containing the same kind of peptide fragment, wherein the amino-acid composition of the peptide before fragmentation or the quantities of amino acids in the peptide before fragmentation is deduced based on a result of an analysis performed on each of the peptide fragments separately collected in the separation step.

The method for analyzing a protein or peptide according to the first mode of the present invention is characterized in that: the peptide originating from the analysis target which is either a peptide or a protein is broken down into individual amino acids in the fragmentation step; and the amino acids are separated according to the kinds of amino acids in the separation step and each kind of the separated amino acids is individually subjected to quantitative determination.

In the analyzing method according to the first mode of the present invention, a broad-spectrum endopeptidase is used in place of the conventionally performed acidic hydrolysis in order to completely break down the test peptide into isolated amino acids. The broad-spectrum endopeptidase, which has the function of breaking peptide bonds, is characterized by its non-selectivity in breaking the peptide bonds. Due to such a function of the broad-spectrum endopeptidase, the test peptide is cleaved at various bonding sites, to be eventually broken down into a mixture of amino acids, with all the bonds broken. The subsequent procedure of the analysis can be the same as conventionally known procedures. For example, after the amino acids are separated and collected according to the kinds of amino acids in the separation step, those amino acids can be individually labelled and subjected to an analysis. It is also possible to use an amino-acid analyzer described in Non-Patent Document 2.

The second mode of the method for analyzing a protein or peptide according to the present invention is characterized in that:

in the fragmentation step, the peptide originating from the analysis target which is either a peptide or a protein is broken down into oligopeptides whose amino-acid sequence lengths are shorter than that of the original peptide;

in the separation step, a mixture of the oligopeptides is separated according to the kinds of oligopeptides and collected in the form of fractions, each fraction containing the same kind of oligopeptide;

the method further includes a fragment composition deduction step, in which mass spectrum data are obtained by performing a mass spectrometry on each of the oligopeptides separated in the separation step and in which an amino-acid composition of each oligopeptide is deduced based on the mass spectrum data; and the amino-acid composition of the peptide before fragmentation or the quantities of the amino acids in the peptide before fragmentation are determined based on the deduced amino-acid compositions of the oligopeptides.

The system for analyzing a protein or peptide according to the present invention is a system for embodying the analyzing method according to the second mode of the present invention. Specifically, it is a system for analyzing a protein or peptide for determining at least an amino-acid composition of a protein or peptide or quantities of amino acids in a protein or peptide by mass spectrometry, including:

a) a fragmentation section for breaking down a test peptide originating from the analysis target which is either a peptide or a protein into oligopeptides whose amino-acid sequence lengths are shorter than that of the test peptide by breaking peptide bonds using a broad-spectrum endopeptidase;

b) a separation section for separating a mixture of the oligopeptides obtained by the fragmentation section according to the kinds of oligopeptides, and for collecting the oligopeptides in the form of fractions, each fraction containing the same kind of peptide fragment;

c) a mass spectrometry section for obtaining mass spectrum data by performing a mass spectrometry on each of the oligopeptides separated by the separation section; and d) a fragment composition deduction section for deducing an amino-acid composition of each oligopeptide based on the mass spectrum data obtained by the mass spectrometry section, wherein the amino-acid composition of the peptide before fragmentation or the quantities of the amino acids in the peptide before fragmentation are determined based on the amino-acid compositions of the oligopeptides deduced by the fragment composition deduction section.

In the analyzing method according to the second mode of the present invention carried out by the present analyzing system, the digestive break down of the test peptide using a broad-spectrum endopeptidase is intentionally stopped at the level of oligopeptides whose length in terms of the number of amino acids is within a range from a few up to ten (more or less). This is different from the conventional method in which the test peptide is completely broken down into isolated amino acids by acidic hydrolysis or other processes. As already stated, the test peptide is cleaved at various bonding sites due to the action of the broad-spectrum endopeptidase, so that various kinds of oligopeptides with different amino-acid sequences are produced.

In the separation step, for example, the sample which has been temporally separated by liquid chromatography (normally, reversed-phase chromatography) is divided into fractions by means of a fraction collector, and those fractions are individually put onto a multiwell plate or the like. Thus, the mixture of various kinds of oligopeptides obtained in the fragmentation step is separated and collected in the form of fractions, each of which contains the same kind of oligopeptide. In the fragment composition deduction step, the separated oligopeptides are individually supplied to a mass spectrometer to acquire mass spectrum data for each oligopeptide. From the mass spectrum, the actual mass of the oligopeptide is calculated, and based on this mass, the kinds and numbers of amino acids constituting the oligopeptide (i.e. the composition of the oligopeptide) are deduced. After the amino-acid compositions of all the oligopeptides originating from the original peptide are determined, the amino-acid composition of the original peptide can be deduced by summing up the compositions of the oligopeptides.

Once the amino-acid compositions of all the oligopeptides produced by the fragmentation have been revealed, it may be possible to deduce the amino-acid sequence of the original peptide by appropriately combining the amino-acid sequences of the oligopeptides, since the amino-acid sequence of each individual oligopeptide corresponds to a portion of the amino-acid sequence of the original peptide.

Accordingly, the method for analyzing a protein or peptide according to the second mode of the present invention may further include a sequence deduction step, in which the amino-acid sequence of the test peptide is deduced based on the amino-acid sequence of each of the oligopeptides deduced in the fragment composition deduction step, by combining different oligopeptides while making use of common sequence patterns located in end portions of a plurality of amino-acid sequences.

In this case, the characteristic of the enzyme used in the fragmentation step, i.e. the non-selective breaking of the peptide bonds, works effectively. That is to say, once a wide variety of oligopeptides having different amino-acid sequences originating from one kind of peptide have been obtained, it is possible that there are oligopeptides which differ from each other in terms of the entire amino-acid sequence and in which the same amino-acid sequence pattern corresponding one portion of the original peptide is located in the end portion of each oligopeptide. Furthermore, if the same amino-acid sequence pattern is present at one end of one kind of oligopeptide as well as in the opposite end of another kind of oligopeptide, it is likely that a peptide obtained by combining the two oligopeptides with the common sequence patterns overlapped with each other corresponds to a portion of the original peptide. Accordingly, in the sequence deduction step, the amino-acid sequence of the original peptide is deduced by repeating the steps of searching the deduced amino-acid sequences of the oligopeptides for the aforementioned kind of overlapping portions and combining any oligopeptides that can be combined through such overlapping portions.

Combining a plurality of oligopeptides probably yields a considerable number of candidates of the amino-acid sequence of the original peptide. To select reliable sequences from those candidates, it is preferable to use the mass of the original peptide calculated from a result of a mass spectrometry of this peptide.

Thus, in the method for analyzing a protein or peptide according to the second mode of the present invention:

a peptide information collection step is further provided, in which a mass spectrometry on the peptide before being fragmented in the fragmentation step is performed to obtain mass spectrum data, and in which the mass of the peptide is calculated from the mass spectrum data; and in the sequence deduction step, a peptide mass calculated from each of the deduced amino-acid sequences of the peptides is compared with the peptide mass calculated in the peptide information collection step to determine whether or not the deduction of the amino-acid sequence is appropriate.

This method improves the probability of a correct deduction of the amino-acid sequence covering the entire length of the original peptide before fragmentation.

If the original peptide before fragmentation is excessively long (e.g. if its length is comparable to that of a protein), it is most likely that the number of possible candidates of the amino-acid sequence becomes too large to practically obtain a proper result. To avoid such a situation, the entire length of the peptide to be fragmented should preferably be limited to an appropriate length.

Accordingly, the method for analyzing a protein or peptide according to the present invention may further include:

a pre-cleavage step, which is performed before the fragmentation step to obtain polypeptides having limited lengths of amino-acid sequences by cleaving the analysis target which is either a peptide or a protein; and a pre-separation step, in which a mixture of the polypeptides obtained in the pre-cleavage step is separated and collected in the form of fractions, each of which contains the same kind of polypeptide, and the processes of the fragmentation step and subsequent steps are performed for each of the polypeptides separated in the pre-separation step.

By this method, the number of oligopeptides resulting from the fragmentation is moderately limited. Therefore, in the process of combining two amino-acid sequence candidates deduced from the amino-acid compositions of the oligopeptides, even if one or both of those amino-acid sequences are incorrect, it is less likely that an overlapping portion accidentally exists in the two sequences and causes a false-positive combination. As a result, the number of amino-acid sequence candidates for the original peptide decreases, and a correct result is more likely to be obtained.

As already noted, one preferable example of the broad-spectrum endopeptidase is proteinase K. Proteinase K has an extremely low degree of substrate specificity and can non-selectively break peptide bonds efficiently. Furthermore, its reaction rate is high. Another advantage is that proteinase K is readily available as well as easy to handle since it is widely used for removing contaminants from a nucleic-acid preparation in the field of biochemistry.

To promote the fragmentation of peptides by the broad-spectrum endopeptidase so as to maximally shorten the reaction time in the fragmentation step, it is preferable, for example, to make the broad-spectrum endopeptidase act on the test peptide under a predetermined temperature higher than normal temperature (e.g. within a range from 50 to 60 degrees Celsius).

The fragmentation of the test peptide may also be promoted by a supplementary use of a fine ultrasonic vibration. Combining these techniques will even more promote the fragmentation of the peptides.

By using such techniques, it is possible to reduce the amount of time required for the break down of peptides into isolated amino-acids or oligopeptides and improve the throughput of the analysis of a protein or peptide.

Effect of the Invention

With the method and system for analyzing a protein or peptide according to the present invention, information on cysteine and other amino acids that will be broken or modified if subjected to acidic hydrolysis can also assuredly be obtained, since the pretreatment for breaking down a peptide into analyzable fragments does not use acidic hydrolysis. More specifically, any kinds of amino acids other than leucine and isoleucine (which have the same mass and are indistinguishable) can be identified, so that an amino-acid composition and/or the quantities of amino acids can be determined with high accuracy.

The break down of a peptide using proteinase K or similar broad-spectrum endopeptidase is considerably easier than the conventional techniques, such as the acidic hydrolysis or the break down using a plurality of digestive enzymes. The task requires no special skills or experience and hence can be conducted even by a person with insufficient experience or skill in the task. Incorrect operations or difficulties are less likely to occur. An advantage also exists in terms of the analysis cost since no special apparatus or device is required for the break down of the peptides.

In particular, the analyzing method according to the second mode of the present invention is advantageous for improving the throughput of the analysis since it does not require a peptide to be completely broken down into isolated amino acids and hence needs a shorter period of time for the pretreatment. In the conventional methods, in which calibration curves are used to convert label-signal intensity (which reflects the amount of amino acid) into concentration (which reflects the number of molecules of the amino acid), it is necessary to perform a measurement of an internal standard sample for creating the calibration curves along with the measurement of the target sample. By contrast, in the analyzing method according to the second mode of the present invention, since the number of molecules of each amino acid in the amino-acid sequence of the original peptide or an oligopeptide is determined based on a result of a mass spectrometry, no measurement of an internal standard sample is necessary. This is also advantageous for simplifying the analyzing task.

BRIEF DESCRIPTION OF THE DRAWINGS

FIG. 3 is an illustration showing the process of combining amino-acid sequence candidates in the amino-acid sequence analyzing method of the present embodiment.

FIG. 4 shows (a) one example of peptides obtained by breaking down insulin with a digestive enzyme, and (b) one example of the amino-acid sequences and amino-acid compositions of oligopeptides obtained by fragmenting one of the aforementioned peptides using proteinase K.

FIG. 7 illustrates a process of combining the peptide fragments shown in FIG. 6.

FIG. 8 shows examples of amino-acid sequence candidates obtained by combining the amino-acid sequence candidates shown in FIG. 4(b).

FIG. 9 is a flowchart showing a conventional and common used procedure of a quantitative analysis of amino acids in a protein.

MODE FOR CARRYING OUT THE INVENTION

An amino-acid sequence analyzing method which is one embodiment of the present invention, as well as an amino-acid sequence analyzing system for carrying out the method, are hereinafter described with reference to the attached drawings.

Figure 1:
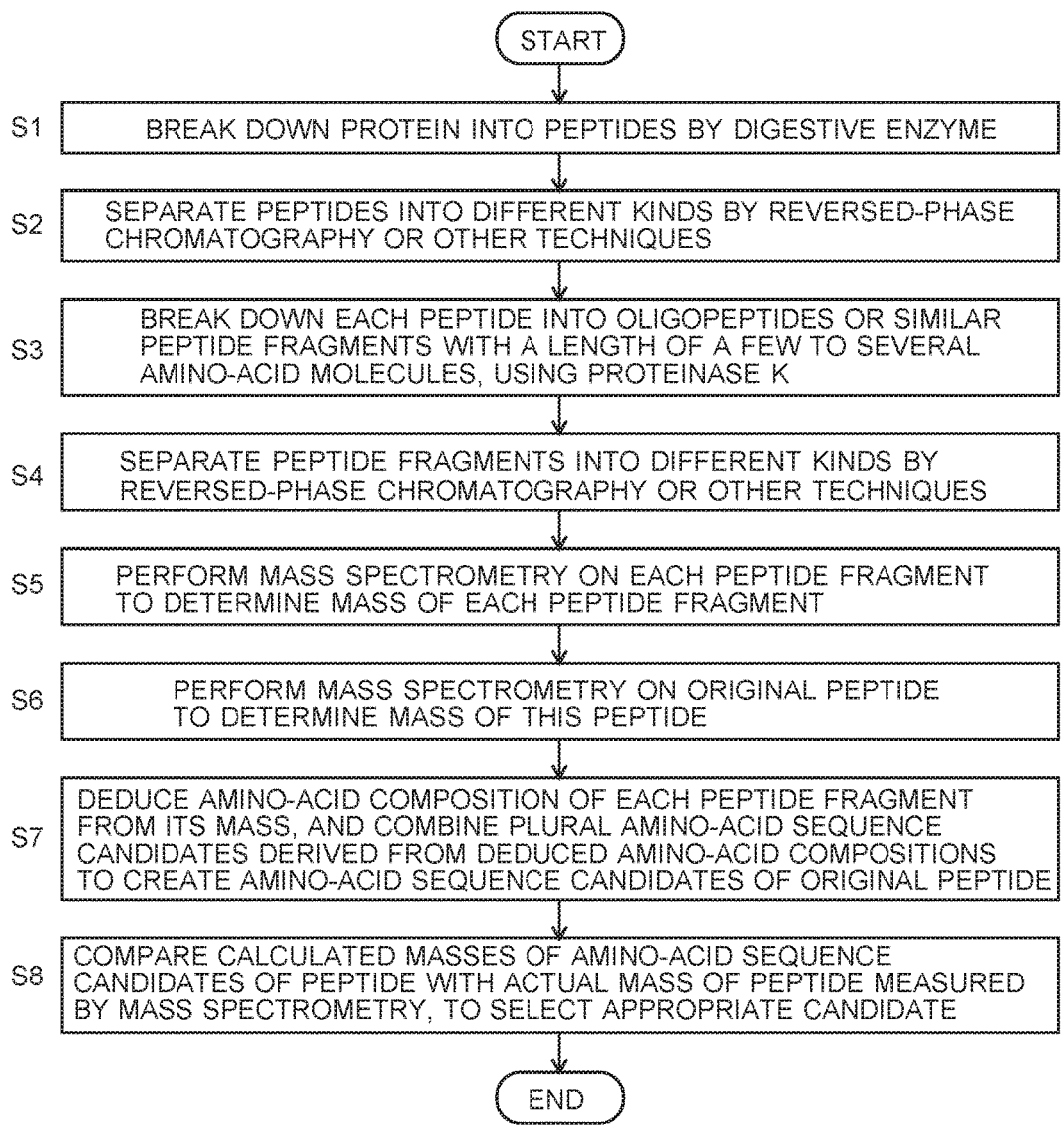
FIG. 1 is a flowchart showing the steps of the tasks and processes of an amino-acid sequence analyzing method which is one embodiment of the present invention.
Figure 2:
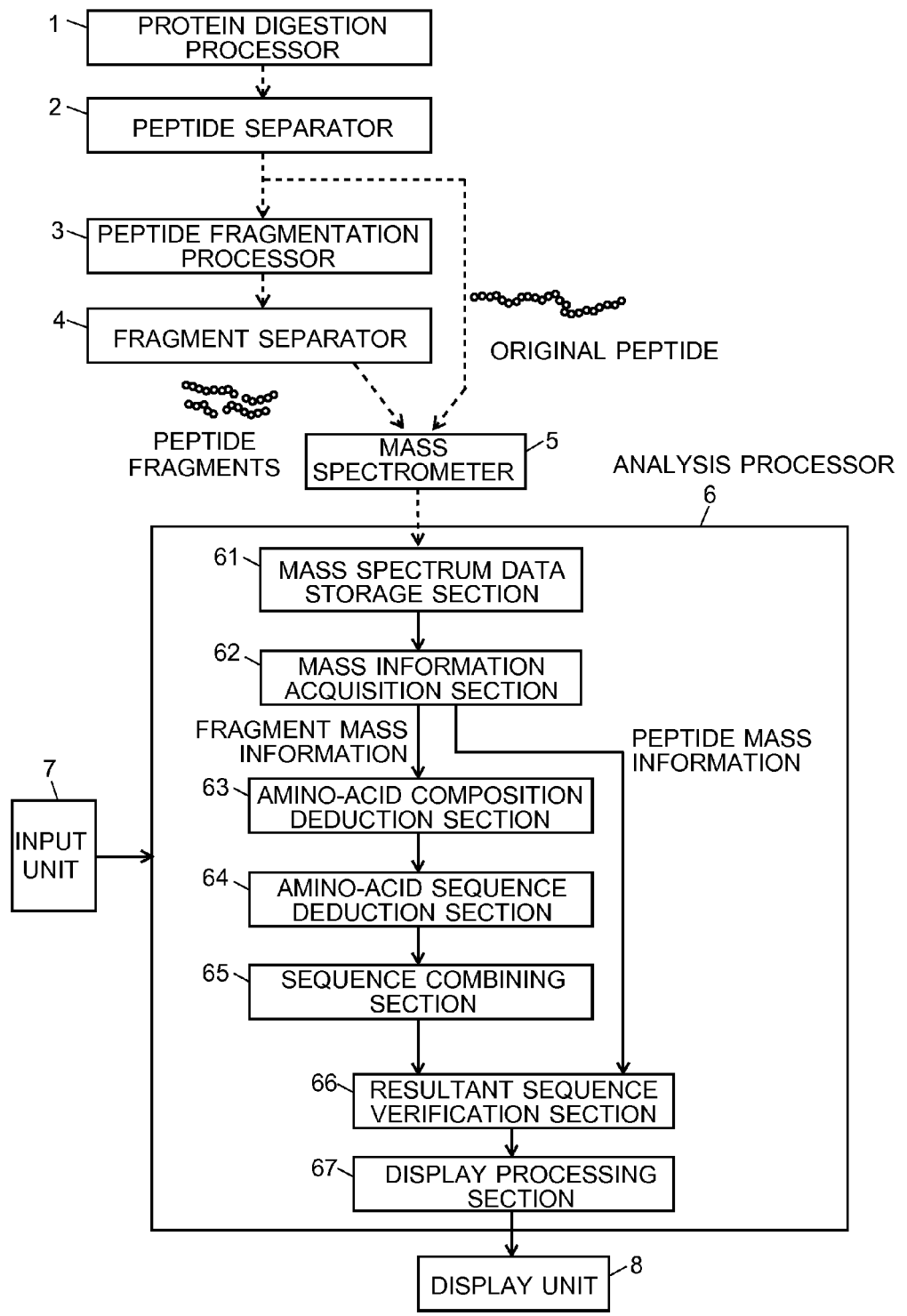
FIG. 2 is a block configuration diagram of an amino-acid sequence analyzing system for carrying out the amino-acid sequence analyzing method shown in FIG. 1.

FIG. 1 is a flowchart showing the steps of the tasks and processes of the amino-acid sequence analyzing method according to the present embodiment. FIG. 2 is a schematic configuration diagram of the amino-acid sequence analyzing system according to the present embodiment.

As shown in FIG. 2, the amino-acid sequence analyzing system according to the present embodiment includes a protein digestion processor 1, a peptide separator 2, a peptide fragmentation processor 3, a fragment separator 4, a mass spectrometer 5, an analysis processor 6 as well as an input unit 7 and a display unit 8 which are annexed to the analysis processor 6.

The protein digestion processor 1 may include an incubator for maintaining the temperature of a solution containing a protein (or a peptide consisting of a long sequence of amino acids) as a sample to be analyzed, with a digestive enzyme added.

The peptide separator 2 may include, for example, a liquid chromatograph having a reversed-phase column, a fraction collector for fractionating various kinds of peptides separated by the reversed-phase column and for placing the obtained fractions onto a multiwell plate, and other elements.

The peptide fragmentation processor 3 may include, for example, a column packed with beads or similar support materials on which a broad-spectrum endopeptidase is fixed, a passage system for repeatedly (cyclically) passing a peptide solution through the column, and other elements.

The fragment separator 4 may have a configuration similar to the peptide separator 2 and include, for example, a liquid chromatograph with a reverse-phase column, a fraction collector and other elements.

The mass spectrometer 5 is, for example, a matrix assisted laser desorption/ionization time-of-flight mass spectrometer (MALDI-TOFMS). Naturally, this is not the only possible choice of the mass spectrometer 5.

The analysis processor 6, which analyzes and processes data obtained by the mass spectrometer 5, includes a mass spectrum data storage section 61, a mass information acquisition section 62, an amino-acid composition deduction section 63, an amino-acid sequence deduction section 64, a sequence combining section 65, a resultant sequence verification section 66, a display processing section 67 and other functional blocks. The substance of the analysis processor 6 is a personal computer or workstation on which a dedicated analyzing program is executed to implement the aforementioned functions. The program may be read from various kinds of record media, such as a removable record medium (e.g. CD-ROM, CD-R, CD-RW, MO, DVD-RAM or memory card) or a record medium which is normally non-removable (e.g. HDD). It may also be retrieved from an external source via communication lines.

A procedure of the amino-acid sequence analyzing method which is performed using the amino-acid sequence analyzing system having the previously described configuration is hereinafter described along with the flowchart shown in FIG. 1.

In the protein digestion processor 1, the peptide bonds in a protein (which is the sample) are broken using an appropriate kind of digestive enzyme to produce a mixture of peptides having certain lengths (polypeptides) (Step S1). For example, in the case where insulin (which is a kind of peptide hormone) is cleaved using trypsin as the digestive enzyme, the peptides having the amino-acid sequences as shown in FIG. 4(*a*) will be obtained. In this example, the longest peptide has a length of approximately 40 in terms of the number of molecules of the amino acids. Cleaving the sample into peptides whose lengths are approximately several tens of amino acids is sufficient for normal purposes. The reason for breaking peptide bonds in advance of peptide fragmentation (which will be described later) is that, if an extremely long protein is directly subjected to the processes of Step S2 and subsequent steps, the number of amino-acid composition candidates to be eventually obtained is most likely to be too large. By breaking the peptide bonds in Step S1, the lengths of the peptides are moderately limited, whereby the probability of such a problem is considerably lowered.

The peptide mixture obtained by enzymatic digestion in the previously described manner contains various kinds of peptides. Those peptides are separated by the peptide separator 2 into fractions, each of which contains one kind of peptide (Step S2). The techniques used in this step, i.e. the reversed-phase chromatography and the fraction collector for placing fractionated peptides on a multiwell plate, are frequently used in normal biochemical measurements and extremely common. The processes of Step S3 and subsequent steps are performed for each of the isolated peptide species.

Subsequently, in the peptide fragmentation processor 3, various bonding sites in one peptide species are broken by means of a broad-spectrum endopeptidase to produce a mixture of peptide fragments (oligopeptides) whose lengths are within a range from a few to ten in terms of the number of molecules of the amino acids (Step S3). The broad-spectrum endopeptidase used in the present example is proteinase K, which is the most preferable enzyme. As already explained, the reason why proteinase K is preferable is because it has an extremely wide range of substrate specificity and can break all peptide bonds at considerably high reaction rates.

The lengths of the various oligopeptides produced by the fragmentation process in Step S3 do not need to be equal or close to each other as long as the amino-acid composition of each oligopeptide can be accurately deduced based on a result of mass spectrometry (which will be described later). However, excessively long or extremely short amino-acid sequences are inappropriate for the bonding process which uses an overlapping portion of the amino-acid sequences (as will be described later); in particular, completely breaking down peptides into isolated amino acids (i.e. individual amino acids) as in the conventional case must be avoided. Accordingly, for example, it is preferable to perform a preliminary experiment of the fragmentation using proteinase K for a plurality of kinds of peptides, to measure a period of time for breaking down each peptide into fragments of appropriate lengths, and to determine the reaction process time with reference to the measured result.

If a column packed with support materials on which proteinase K is fixed as described earlier is used as the peptide fragmentation processor 3, it is possible to construct a passage system which makes a peptide solution circulate through one or a plurality of columns, or to use a column which itself has a circular shape, so that the reaction process time can be adjusted by changing the number of circulations of the peptide solution through the circulating passage or the circular column. Such a configuration using a column also has the effect of preventing proteinase K from being mixed with the substrate (i.e. peptide) as well as suppressing the autolysis of proteinase K.

It is also possible to determine the end point of the reaction process by a real-time measurement instead of previously setting the reaction process time in the previously described manner. A specific example is as follows: A solution resulting from a digestive reaction catalyzed by proteinase K is subjected to a measurement using an appropriate method (e.g. a light-scattering method), and based on the measured result, the molecular weights of the peptides in the solution are roughly deduced in real time. From the deduced molecular weights, the length of the amino-acid sequence of the peptides is deduced. The reaction is discontinued when the deduced length has become equal to or shorter than a predetermined length of the amino-acid sequence.

To promote the peptide fragmentation process using the broad-spectrum endopeptidase, it is possible to heat the solution to appropriate temperatures (e.g. 50-60 degrees Celsius) or apply a fine ultrasonic vibration. By appropriately combining these techniques, the period of time required for the peptide fragmentation can be shortened to approximately one hour, or even shorter in some cases. The fragmentation can be completed in a dramatically shorter period of time than the conventional method of breaking down polypeptides into isolated amino acids by acidic hydrolysis.

FIG. 4(b) shows one example of the peptide fragments obtained by performing the peptide fragmentation process on the peptide [GFFYTPK] (SEQ. ID No. 4), which is one of the tryptic digests from insulin shown in FIG. 4(a). It should naturally be understood that what is actually known at this stage is the mere fact that the target of fragmentation is a certain kind of peptide; even the amino-acid composition of the peptide before fragmentation is still unknown, much less its amino-acid sequence.

The peptide-fragment mixture contains various peptide fragments originating from one kind of peptide. In the fragment separator 4, those peptide fragments are separated into fractions each of which contains one kind of peptide (Step S4). In the example of FIG. 4(b), four kinds of peptide fragments are individually prepared as separate samples.

Those samples, each of which contains one kind of peptide fragment have been prepared, are individually subjected to mass spectrometry in the mass spectrometer 5. The obtained mass spectrum data are sent to the analysis processor 6, to be stored in the mass spectrum data storage section 61. For each peptide fragment, the mass information acquisition section 62 reads the corresponding data from the mass spectrum data storage section 61, creates a mass spectrum and performs peak detection. Then, the mass information acquisition section 62 extracts molecular ion peaks from the detected peaks and determines the mass of the peptide fragment based on the mass-to-charge ratios of the extracted peaks (Step S5). Such a process of determining the mass of a peptide fragment based on a result of mass spectrometry is similarly performed for each of a large number of peptide fragments originating from one kind of polypeptide.

Meanwhile, a mass spectrometry for the polypeptide before the peptide fragmentation process is also performed using the mass spectrometer 5, and based on the acquired mass spectrum data, the mass of the polypeptide is obtained (Step S6). Step S6 can be performed at any timing within a time range from Step S3 to immediately before Step S8.

The mass information of the peptide fragments is sent to the amino-acid composition deduction section 63. For each peptide fragment, the amino-acid composition deduction section 63 deduces the amino-acid composition (i.e. the kinds of amino acids constituting the peptide fragment as well as the number of molecules of each amino acid) which matches the given mass, using the accurate mass information of the known kinds of amino acids. To improve the accuracy of the deduction of the amino-acid composition, it is preferable to use a mass spectrometer 5 with high mass accuracy. In this respect, the mass spectrometer 5 should preferably be a time-of-flight mass spectrometer, since this type of device is generally capable of measurements with high mass accuracy. Among the twenty kinds of amino acids which are known as the constituents of proteins, leucine and isoleucine have the same mass-to-charge ratio and are mutually indistinguishable based on their mass. If the presence of a substance which matches the mass of those two amino acids has been deduced, that substance can be identified as either leucine or isoleucine.

What is shown on the right side of the amino-acid sequences of the peptide fragments in FIG. 4(b) is the amino-acid compositions calculated from the masses of the respective peptide fragments. For example, the amino-acid composition of the peptide fragment with the amino-acid sequence [GFFY] (SEQ. ID No. 7) is "two molecules of amino acid F, one molecule of amino acid G and one molecule of amino acid Y." For the peptide fragment with the amino-acid sequence [FYTP] (SEQ. ID No. 21), the amino-acid composition is "one molecule of amino acid F, one molecule of amino acid Y, one molecule of amino acid T and one molecule of amino acid P." It is those amino-acid compositions that can be determined with high reliability from the results of the mass spectrometry. If it is only the amino-acid composition of the original peptide that needs to be determined, the remaining task is to simply sum up the information on the deduced amino-acid compositions of the respective peptide fragments. If an attempt should be made to deduce the amino-acid sequence, the following process will subsequently be performed.

After the amino-acid compositions of the respective peptide fragments are obtained, the amino-acid sequence deduction section 64 derives all amino-acid sequences that can be obtained from each of the amino-acid compositions. FIG. 5(a) shows all the amino-acid sequences that can be derived from the amino-acid composition "F2G1Y1" shown in FIG. 4(b), while FIG. 5(b) shows a portion of the amino-acid sequences that can be derived from the amino-acid composition "F1Y1T1P1" shown in FIG. 4(b). These examples demonstrate that a considerable number of amino-acid sequence candidates will normally be derived from one amino-acid composition.

Figures 5, 6:
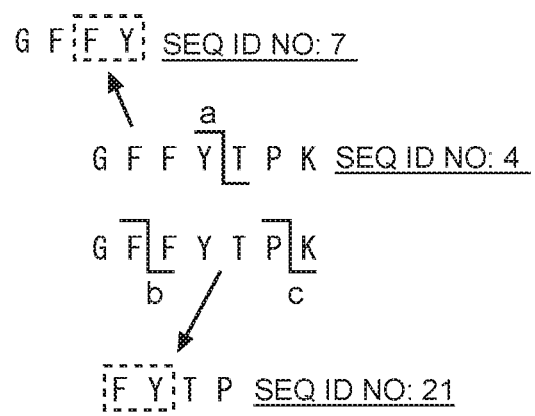
FIG. 5 shows examples of amino-acid sequence candidates derived from the amino-acid compositions shown in FIG. 4(b).
FIG. 6 shows one example of the peptide fragmentation shown in FIG. 4(b).

As explained earlier, in the peptide fragmentation process of Step S3, the bonds in one polypeptide are broken non-selectively, i.e. indiscriminately. FIG. 6 shows one example of the peptide fragmentation shown in FIG. 4(b). If the polypeptide with an amino-acid sequence of [GFFYTPK] (SEQ. ID No. 4)is cleaved at position "a" in FIG. 6, a peptide fragment with an amino-acid sequence of [GFFY] (SEQ. ID No. 7) is produced. If the same heptapeptide is cleaved at positions "b" and "c", a peptide fragment with an amino-acid sequence of [FYTP] (SEQ. ID No. 21) is produced. In those peptide fragments, the amino-acid sequence pattern [FY] corresponds to the same portion of the original polypeptide. Thus, when the cleavage non-selectively occurs at any bonding site, the same amino-acid sequence pattern (which may consist of a single amino acid) can occur at one end of one peptide fragment as well as at the opposite end of another peptide fragment. This fact is utilized in the present method to combine amino-acid sequence candidates of the peptide fragments.

FIG. 3 illustrates the method of combining amino-acid sequence candidates. For one amino-acid sequence candidate deduced from one peptide fragment, the other amino-acid sequence candidates deduced from the other peptide candidates are searched for an amino-acid sequence candidate which has an overlapping portion, i.e. an amino-acid sequence pattern which matches an amino-acid sequence pattern at one end of the amino-acid sequence candidate under investigation. If an amino-acid sequence candidate with an overlapping portion has been found, the two amino-acid sequence candidates are combined with each other, using the overlapping portion as the "tag for sticking", to form a new amino-acid sequence candidate having a longer sequence. In principle, the amino-acid sequence is further extended by repeating such a binding process.

FIG. 7 illustrates the process of combining the peptide fragments shown in FIG. 6. A comparison between [GFFY] (SEQ. ID No. 7) (one of the amino-acid sequence candidates corresponding to one peptide fragment) and [FYTP] (SEQ. ID No. 21) (one of the amino-acid sequence candidates corresponding to another peptide fragment) reveals that the sequence pattern "FY" is common to the two candidates; i.e.

the former candidate has the pattern at its right-hand end while the latter has the pattern at its left-hand end. Using this pattern as the tag of sticking, the two candidates can be combined together to obtain a new amino-acid sequence candidate expressed as [GFFYTP] (SEQ. ID No. 25). Naturally, in this binding stage, it is impossible to know whether or not the new candidate is a correct result.

FIG. 8 shows a list of amino-acid sequence candidates produced by attempting the binding process via an overlapping portion for each possible combination of the first three amino-acid sequence candidates corresponding to the amino-acid composition "F2G1Y1" shown in FIG. 5(a) and all the amino-acid sequence candidates corresponding to the amino-acid composition "F1P1T1Y1" shown in FIG. 5(b). In principle, there is a possibility that a correct result for the original peptide, i.e. a plurality of amino-acid sequence candidates including the correct amino-acid sequence, will eventually be obtained by extending the amino-acid sequence by repeating such a binding process.

However, the previously described process of simply combining the sequences which have been found to have an overlapping portion yields an enormous number of sequence candidates. For example, in the case of a peptide fragment consisting of five amino-acid molecules of different kinds, the number of amino-acid sequence candidates is 5!=120. If, for example, five such peptide fragments are to be combined, the number of amino-acid sequence candidates can amount to a maximum of $120^5$. Such a number is evidently beyond the scope of processing capacity. Therefore, it is preferable to conduct the binding process while performing a pruning process to decrease the number of candidates or prevent an excessive increase in that number.

A specific example of the pruning process is as follows: Consider the case of combining one amino-acid sequence candidate having an amino-acid composition of "F2G1Y1" and another amino-acid sequence candidate having an amino-acid composition of "F1P1T1Y1." Both candidates have one "F" and one "Y" in common, which means that no other amino acids than these two can serve as the "tag for sticking." There are only three possible cases relating to the choice of the tag for sticking: one "F", one "Y" and the combination of one "F" and one "Y." In the case of using one "F" as the tag for sticking, the "Y" in each of the two peptide fragments should be two separate "Ys" which are not included in the overlapping portion. This is one limiting condition on the amino-acid sequence to be obtained by the binding. By imposing such limiting conditions on the amino-acid sequence candidates to be obtained after the binding process, the amino-acid compositions corresponding to the amino-acid sequences produced by the binding process in the three aforementioned cases can be revealed as "F2G1P1T1Y2", "F3G1P1T1Y1" and "F2G1P1T1Y1", respectively. Indeed, any of the amino-acid sequences shown in the example of FIG. 8 has one of these three amino-acid compositions.

By performing the pruning process under the limiting conditions, the amount of computation by the sequence combining section 65 can dramatically be reduced, and ultimately, one or more amino-acid sequence candidates, each of which consists of all the peptide fragments combined together or contains all the peptide fragments in a consistent form, will be obtained (Step S7). The obtained amino-acid sequence candidates are sent to the resultant sequence verification section 66.

Meanwhile, the mass of the polypeptide measured in Step S6 is also sent from the mass information acquisition section 62 to the resultant sequence verification section 66. The resultant sequence verification section 66 processes the provided information as follows: For each of the plurality of amino-acid sequence candidates, the mass of the amino-acid sequence is calculated from the kinds of constituent amino acids and the number of molecules of each amino acid. The calculated mass is compared with the measured mass of the polypeptide. If the amino-acid sequence candidate is a correct result, its calculated mass should ideally have zero difference from the measured mass (or actually, only a slight difference within an error range associated with the mass accuracy of the mass spectrometer 5 or other factors). Accordingly, the large number of amino-acid sequence candidates are searched for a candidate whose calculated mass is the closest to the measured value, and this candidate is judged as the correct amino-acid sequence to be selected (Step S8). It is also possible to extract all amino-acid sequence candidates whose calculated masses are within a predetermined range from the measured mass and to select them as probable amino-acid sequences, rather than narrowing the candidates to a single amino-acid sequence.

For each of the polypeptides fractionated in Step S2, the processes of Steps S3 through S8 are performed to calculate one or more amino-acid sequences corresponding to each polypeptide. After the calculation is completed, the display processing section 67 shows the calculated result through the display unit 8. Even if the attempt to deduce an amino-acid sequence has not reached any result or has yielded only an inappropriate result due to some reasons (e.g. due to an excessive amount of computation), it is still possible to display the amino-acid composition of the peptide.

As described thus far, in the amino-acid sequence analyzing method carried out by the amino-acid sequence analyzing system shown in FIG. 2, the amino-acid composition of a polypeptide originating from a target sample can be accurately determined, and furthermore, its amino-acid sequence can also be deduced, by performing a fragmentation process which is easier and less time-consuming than the conventionally and commonly used method which includes a complex, cumbersome and time-consuming pretreatment, such as acidic hydrolysis.

The process performed by the sequence combining section 65 in the amino-acid sequence analyzing system of the previous embodiment uses a portion of the technique described in Japanese Patent Application No. 2012-198301 which was filed earlier by the applicant of the present patent application.

The system of the previous embodiment was designed to deduce not only an amino-acid composition but also an amino-acid sequence by utilizing the characteristics of the peptide break down using a broad-spectrum endopeptidase which is the most characteristic element of the analyzing method according to the present invention. However, in general, it is often the case that an accurate deduction of the amino-acid composition is all that is needed. Furthermore, as already explained, adopting the peptide break down using the broad-spectrum endopeptidase in place of the conventional peptide break down using acidic hydrolysis produces other favorable effects, such as an increase in the number of kinds of detectable amino acids (which means an improved accuracy of the amino-acid composition deduction) and a reduction in the workload on workers. Therefore, for example, replacing the process of Step S51 in the analyzing procedure illustrated in FIG. 9 with the peptide break down using a broad-spectrum endopeptidase will also make a significant advantage over the conventional technique.

That is to say, the previous embodiment is a mere example of the present invention, and any change, modification or addition appropriately made within the spirit of the present invention will naturally be included in the scope of claims of the present patent application.

EXPLANATION OF NUMERALS

1 . . . Protein Digestion Processor
2 . . . Peptide Separator
3 . . . Peptide Fragmentation Processor
4 . . . Fragmentation Separator
5 . . . Mass Spectrometer
6 . . . Analysis Processor
61 . . . Mass Spectrum Data Storage Section
62 . . . Mass Information Acquisition Section
63 . . . Amino-Acid Composition Deduction Section
64 . . . Amino-Acid Sequence Deduction Section
65 . . . Sequence Combining Section
66 . . . Resultant Sequence Verification Section
67 . . . Display Processing Section
7 . . . Input Unit
8 . . . Display Unit

The invention claimed is:

1. A method for analyzing a protein or peptide for determining at least an amino-acid composition of a protein or a peptide, an amino-acid sequence of the protein or the peptide or quantities of amino acids in the protein or the peptide, comprising:
   a) a fragmentation step, in which a peptide originating from an analysis target which is either a peptide or a protein is broken down into peptide fragments by breaking peptide bonds using a broad-spectrum endopeptidase;
   b) a separation step, in which a mixture of the peptide fragments obtained in the fragmentation step is separated according to kinds of peptide fragments and collected in a form of fractions, each fraction containing a same kind of peptide fragment,
   c) a fragment composition deduction step, in which mass spectrum data are obtained by performing a mass spectrometry on each of the peptide fragments separated in the separation step and in which an amino-acid composition of each peptide fragment is deduced based on mass spectrum data; and
   d) a sequence deduction step, in which the amino-acid sequence of the peptide or protein is deduced, based on the amino-acid sequence of each of the peptide fragments deduced in the fragment composition deduction step, by combining different peptide fragments, the different peptide fragments include at least a first peptide fragment, a second peptide fragment, and a third peptide fragment; the first peptide fragment including a sequence pattern located in an end portion of the first peptide fragment that matches a sequence pattern located in a beginning portion of the second peptide fragment, and the second peptide fragment including a sequence pattern located in an end portion of the second peptide fragment that matches a sequence pattern located in a beginning portion of the third peptide fragment;
   wherein the amino-acid composition of the protein or the peptide before fragmentation, the amino-acid sequence of the protein or the peptide or the quantities of amino acids in the protein or the peptide before fragmentation is deduced by performing step (d) for each of the peptide fragments separately collected in the separation step.

2. The method according to claim 1, wherein the peptide fragments are oligopeptides.

3. The method according to claim 1, wherein:
a peptide information collection step is further provided, in which a mass spectrometry on the peptide before being fragmented in the fragmentation step is performed to obtain mass spectrum data, and in which a mass of the peptide is calculated from the mass spectrum data; and
in the sequence deduction step, a peptide mass calculated from each of the deduced amino-acid sequences of the peptides is compared with the peptide mass calculated in the peptide information collection step to determine whether or not a deduction of the amino-acid sequence is appropriate.

4. The method according to claim 1, wherein:
proteinase K is used as the broad-spectrum endopeptidase.

5. The method according to claim 1, wherein:
in the fragmentation step, the broad-spectrum endopeptidase is made to act on the peptide or protein under a temperature from 50 to 60 degrees Celsius.

6. The method according to claim 1, wherein:
in the fragmentation step, the fragmentation of the peptide or protein is promoted by a supplementary use of a fine ultrasonic vibration.

7. The method according to claim 1, further comprising:
a pre-cleavage step, which is performed before the fragmentation step to obtain polypeptides having limited lengths of amino-acid sequences by cleaving the analysis target which is either a peptide or a protein;
a pre-separation step, in which a mixture of the polypeptides obtained in the pre-cleavage step is separated and collected in a form of fractions each of which contains a same kind of polypeptide,
and steps a) to d) are performed for each of the polypeptides separated in the pre-separation step.

* * * * *